United States Patent [19]

Sangokoya

[11] Patent Number: 5,248,801
[45] Date of Patent: Sep. 28, 1993

[54] PREPARATION OF METHYLALUMINOXANES

[75] Inventor: Samuel A. Sangokoya, Baton Rouge, La.

[73] Assignee: Ethyl Corporation, Richmond, Va.

[21] Appl. No.: 935,947

[22] Filed: Aug. 27, 1992

[51] Int. Cl.$^5$ ................................. C07F 5/06
[52] U.S. Cl. .................... 556/179; 556/182; 556/190
[58] Field of Search ............. 556/179, 182, 190, 179, 556/182

[56] References Cited

U.S. PATENT DOCUMENTS

| | | | |
|---|---|---|---|
| 3,135,708 | 6/1964 | Vandenberg | 260/2 |
| 3,152,105 | 10/1964 | Long | 260/88.2 |
| 3,300,458 | 1/1967 | Manyik et al. | 260/88.2 |
| 4,658,078 | 4/1987 | Slaugh et al. | 586/512 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,908,463 | 3/1990 | Bottelberghe | 556/179 |
| 4,924,018 | 5/1990 | Bottelberghe | 556/179 |
| 4,960,878 | 10/1990 | Crapo et al. | 556/179 |
| 4,968,827 | 11/1990 | Davis | 556/179 |
| 5,015,749 | 5/1991 | Schmidt et al. | 556/179 |
| 5,041,585 | 8/1991 | Deavenport et al. | 556/179 |
| 5,084,585 | 1/1992 | Maezawa et al. | 556/179 |

FOREIGN PATENT DOCUMENTS 0279586  8/1988  European Pat. Off. .

Primary Examiner—Jose G. Dees
Assistant Examiner—Porfirio Nazario
Attorney, Agent, or Firm—David M. Bunnell

[57] ABSTRACT

Soluble methylaluminoxane is prepared by reacting water with a solution of an alkylaluminum compound, wherein at least about half the alkyl groups are methyl groups, in a 1:4 to 4:1 by volume aliphatic hydrocarbon/aromatic hydrocarbon solvent mixture, wherein the aliphatic hydrocarbon solvent has a lower boiling point than the aromatic hydrocarbon solvent, so as to form a product solution of methylaluminoxane in said solvent mixture along with insoluble reaction products which can be removed by filtration. The aliphatic solvent can be removed by vaporization to give a concentrated solution of aluminoxane in the aromatic solvent.

10 Claims, No Drawings

PREPARATION OF METHYLALUMINOXANES

This invention relates generally to alkylaluminoxanes and more specifically to a process for preparing soluble methylaluminoxanes.

Vandenberg U.S. Pat. No. 3,135,705 discloses the preparation of organoaluminum-water reaction products in the presence of an inert diluent such as ethers, aromatic hydrocarbons, saturated aliphatic and cycloaliphatic hydrocarbons, and halogenated hydrocarbons and any mixtures thereof and especially saturated aliphatic hydrocarbons in admixture with ethers.

Bottelberghe, U.S. Pat. No. 4,908,463 describes the preparation of methylaluminoxane in which a trimethylaluminum/toluene solution and a xylene/water dispersion are fed to a T-shaped reactor.

A problem associated with free water addition to trimethylaluminum to produce methylaluminoxane solutions in organic solvents is that the solutions usually contain gel and small particles or other marginally soluble components which aggregate to form gel on standing. Even when the solvent is an aromatic hydrocarbon such as toluene and the particles and/or gel are removed by filtration, additional gel can form in the solution after 2 or 3 weeks, especially when originally prepared dilute solutions are concentrated to higher aluminoxane contents which are more economic for storage, shipment and use.

My copending application Ser. No. 07/853,239, filed Mar. 18, 1992 discloses a process for removing gel forming materials from methylaluminoxanes by adding an aliphatic solvent to an aromatic solvent solution of methylaluminoxane to precipitate the gels.

I have now discovered a process for the direct formation of gel free, soluble methylaluminoxanes which also facilitates recycle of unreacted trimethylaluminum precursor to the methylaluminoxane formation reaction.

In accordance with this invention there is provided a process for preparing a methylaluminoxane comprising the steps of (i) reacting water with a solution of an alkylaluminum compound, wherein at least about half of the alkyl groups are methyl groups, in a 1:4 to 4:1 by volume aliphatic hydrocarbon aromatic hydrocarbon solvent mixture, wherein the aliphatic hydrocarbon solvent has a lower boiling point than the aromatic hydrocarbon solvent, so as to form a product solution of methylaluminoxane in said solvent mixture along with unreacted alkylaluminum and insoluble reaction products and (ii) separating the unsoluble reaction products from said product solution.

In one aspect of the process of the invention, all of the solvent can then be removed from the methylaluminoxane product solution to provide an organic solvent soluble, solid methylaluminoxane. In another aspect of the process of the invention, the aliphatic solvent and a portion of the aromatic solvent and unreacted alkylaluminum are removed from said product solution by vaporization to provide a clear, concentrated, stable, aromatic solvent solution of methylaluminoxane.

In a further preferred aspect of the invention, the lower boiling aliphatic solvent is separated by distillation from the mixture of aliphatic solvent, aromatic solvent and alkylaluminum which is removed from the product solution so as to provide a solvent solution of alkylaluminum having a sufficiently high concentration so that it is suitable for recycle to the water-alkylaluminum reaction.

Methylaluminoxanes (MAO's) may exist in the form of linear or cyclic polymers. The methylaluminoxanes preferred for use in olefin polymerization catalysts usually contain about 5 to 40 or more of the repeating units:

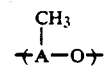

The methylaluminoxanes can contain portions of up to about one half of the total alkyl groups present of $C_2$ to $C_{20}$ alkyl groups and such materials are included within the term "methylaluminoxanes" as used herein. Methylaluminoxanes normally have lower solubility in organic solvents than higher alkylaluminoxanes and the methylaluminoxane solutions tend to be cloudy or gelatinous due to the separation of particles and agglomerates. This problem is frequently encountered with MAO's which have been prepared by adding free water, either neat or contained in a solvent, to a solution of trimethylaluminum as described, for example, in Bottelberghe et al. U.S. Pat. No. 4,908,463 referred to above. According to such processes, the water-alkylaluminum reaction is carried out in an inert solvent. The preferred solvents are aromatic hydrocarbons having carbon numbers of about 6 to 20 such as benzene, toluene, xylene, ethylbenzene, cumene, mesitylene and the like including mixtures thereof. The methylaluminoxane products contain varying amounts of from about 5 to 35 mole percent of the total amount of aluminum value present as unreacted trimethylaluminum.

The process of the invention carries out the water-alkylaluminum reaction in about a 1:4 to 4:1 (preferably about 3:1 to 1:3 and more preferably about 3:1 to 1:1.25) by volume mixture of aliphatic/aromatic solvents, wherein the aliphatic solvent has a boiling point which is sufficiently lower, and preferably at least about 10° C. lower, than the aromatic solvent to permit the aliphatic solvent to be easily removed from the mixed solvent solutions by vacuum flashing or distillation.

Preferred solvents include, but are not limited to, linear and cyclic aliphatic hydrocarbons having from about 5 to 7 carbon atoms, including mixtures thereof. Illustrative, nonlimiting examples of such aliphatic solvents include pentane, isopentane, hexane, cyclohexane, heptane, Isopar C and the like.

The alkylaluminoxane starting material can be pure trimethylaluminum or it can contain portions, for example, about ½ to 1/20 of the total alkyl groups present of higher ($C_2$ to $C_{20}$ and preferably $C_4$ to $C_{10}$), alkyl groups such as is obtained by mixing trimethylaluminum with compounds such as triethylaluminum, tri-n-propylaluminum, tri-n-butylaluminum, triisobutylaluminum, tri-n-hexylaluminum, tri-n-octylaluminum, tri-n-decylaluminum, tri-n-dodecylaluminum, and the like.

The alkylaluminum starting material can be hydrolyzed by reacting it with water which can be in the form of, for example, either free water (neat or contained in a solvent), solid hydrates and/or porous materials which contain imbibed water. Because it is easier to control the reaction, the free water is preferably added in the form of a solution or a dispersion in an organic solvent. However, an advantage of using the mixed solvent system is that loss of aluminum values due to overreaction is minimized and even free water can be used with good (control and moderate cooling to −25° C. Hydrates can even be used at room temperature. Suitable hydrates include salt hydrates such as, for example, $CuSO_4 \cdot 5H_2O$, $Al_2(SO_4)_3 \cdot 18H_2O$, $FeSO_4 \cdot 7H_2O$, $AlCl_3 \cdot 6H_2O$, $Al(NO_3)_3 \cdot 9H_2O$, $MgSO_4 \cdot 7H_2O$, $ZnSO_4 \cdot 7H_2O$, $Na_2SO_4 \cdot 10H_2O$, $Na_3PO_4 \cdot 12H_2O$, $LiBr \cdot 2H_2O$, $LiCl \cdot 1H_2O$, $LiI \cdot 3H_2O$, $KF \cdot 2H_2O$, $NaBr \cdot 2H_2O$ and the like and alkali or alkaline earth metal hydroxide hydrates such as, for example, $NaOH \cdot 1H_2O$, $NaOH \cdot 2H_2O$, $Ba(OH)_2 \cdot 8H_2O$, $KOH \cdot 2H_2O$, $CsOH \cdot 1H_2O$, $LiOH \cdot 1H_2O$ and the like. Mixtures of any of the above hydrates can be used.

The mole ratios of free water or water in the hydrate to total alkylaluminum compound can vary widely, such as for example, from about 2:1 to 1:4 with ratios of from about 1:1 to 1:2 being preferred.

The alkylaluminum-water reaction can be carried out as known in the art in any apparatus which provides good and rapid mixing of the reactants such as, for example an agitator equipped vessel, a falling film reactor, a packed column or a tubular reactor. Suitable reaction temperatures can range from about $-30°$ to $60°$ C. and preferably $-10°$ to $25°$ C. Reaction times are selected to maximize yields and times of about 1 to 5 hours are preferred. Longer times can be used but may be detrimental to yields.

The amount of solvent used in forming the mixture is chosen to permit satisfactory temperature control during the hydrolysis reaction and to minimize the formation of aluminum oxide derivatives which precipitate and are difficult to filter. Generally an amount of solvent to provide concentrations of from about 3 to 20 weight percent of alkylaluminum, based on the total weight of solution, are used.

The presence of the alkane solvent has been found to minimize emulsion formation and to facilitate the removal of precipitated solids from the reaction by filtration, centrifugation, decantation or other solid-liquid separation techniques. Furthermore, the more sparingly soluble aluminoxane compounds precipitate from the reaction mixture so that the product methylaluminoxane solution has less tendency to form gels during prolonged storage than those prepared in aromatic solvents alone. The lower boiling alkane solvent can be easily vacuum stripped or distilled at mild temperatures to form a more concentrated (for example, about 10 to 40 wt. %) aromatic solvent product solution of methylaluminoxane.

The stripping process is also used to remove a portion of the unreacted alkylaluminum. During this process some of the aromatic hydrocarbon is also removed. If only aromatic solvent were used, then the resulting aromatic solvent solution of unreacted alkylaluminum is too dilute to recycle as is and is difficult to concentrate. However, with the process of the invention the lower boiling aliphatic solvent can be easily distilled from the mixture to leave a solution of alkylaluminum in aromatic solvent of sufficient concentration for recycle to the water reaction.

The methylaluminoxanes produced by the process of the invention are termed to be soluble in that after further concentration they provide clear solutions at a concentration by weight of aluminum values of at least 15 grams per 100 g of toluene from which no solids or gels separate for at least 6 months when stored at about $25°$ C.

The invention is further illustrated by, but is not intended to be limited to, the following examples.

The following examples were carried out under inert atmosphere conditions, using Schlenk glassware and vacuum line, in conjunction with an inert gas (nitrogen) dry box. Solvents were dried using standard methods. Filtration and vacuum distillation were done inside the inert gas (nitrogen) dry box and distillates were collected in a trap at $-78°$ C.

EXAMPLE 1

A solution of TMA (20 ml, 14.96 g, 0.2076 mol) in toluene (150 ml) and hexane (150 ml) was placed in a 4-neck flask equipped with mechanical stirrer, temperature probe inlet, condenser and solid addition inlet. While stirring at room temperature, lithium hydroxide monohydrate powder (6.6 g, 0.157 mol) was added during a period of about one hour. The reaction temperature rose to about $28°$ C. The mixture was allowed to cool down slowly to room temperature overnight. This was deliberately done in order to examine the effect of longer reaction time.

After filtration, the clear solution contained 122 mmol aluminum which is equivalent to about 61% of the original aluminum value. The solid product obtained by evaporation is found to be very soluble in toluene (3 grams in 10 g of toluene gave a clear solution).

EXAMPLE 2

The reaction was carried out as described in Example 1 except that the total reaction time was two hours.

The process using the shorter reaction time (i.e. after solid addition) gave better aluminum value recovery (Table 1). The final solid product is also very soluble in toluene).

EXAMPLE 3

Example 3 was carried out to investigate the effect of higher TMA concentration. TMA (100 ml, 74.78 g, 1.037 mol) was dissolved in toluene (300 ml) and hexane (100 ml). The mixture was mechanically stirred and then lithium hydroxide monohydrate (32.7 g, 0.778 mol) was slowly added via the solid addition funnel. Total addition time was about 3 hours. The reaction temperature rose as high as $42°$ C. and then quickly dropped at the end of addition period. The liquid product was transferred via cannula into another flask and then brought into a dry-box for filtration.

The liquid product contained 80% of the original aluminum value. This was evaporated under vacuum to give toluene soluble, free flowing solid.

EXAMPLE 4

To a mixed solvent system, toluene (300 ml) and hexane (300 ml) was added TMA (20 ml, 4.96 g, 0.2075 mol). After cooling to $-25°$ C., water (3 g, 0.16 mol) was added initially through a glass frit (plugged) and then a pump syringe. The reaction period was 5 hours. After filtration, the clear liquid product contained 74% of the original aluminum value.

EXAMPLE 5

This reaction was carried out as described in Example 4, except that the reaction temperature was allowed to warm slowly to room temperature overnight. This total reaction time was about 20 hours. Only about 38% of the starting aluminum value was recovered in the clear liquid product. The longer reaction time period is , therefore, somewhat detrimental to the product yield.

EXAMPLE 6

The effect of increased hexane solvent was tested in this reaction. The experiment was carried out as described in Example 5, except that the solvent molar ratio was 150/450 in favor of hexane solvent. The final mixture was easier to filter. The clear filtrate contained 59% of the original aluminum value and remained gel free after 2 months.

EXAMPLE 7

Water (3 g, 160 mmol) was added slowly via pump syringe to TMA (200 mmol) in a mixture of toluene/isopentane (360/240). The TMA solution was first cooled at −25° C. Total reaction time was 5 hours. After filtration, the clear colorless filtrate contained 65% of the original aluminum value and did not show any gelation sign for over 12 weeks.

STRIPPING OF PRODUCT SOLUTION 414 g of product solution containing 129 mmol Al was stripped at 40° C. and 10 mm Hg for a period of about 2 hours to a concentrated solution containing 89 mmol Al. Since MAO is not volatile, the lost aluminum value is assigned to unreacted $Me_3Al$ (40 mmol Al). This is contained in a mixture of toluene (bp=110° C.) and isopentane (bp=30° C.) which is mainly isopentane. Fractional distillation at moderate temperature and ordinary pressure is expected to remove most of the isopentane (bp=30° C.) and thereby leaving a concentrated solution of TMA in toluene, which is therefore available for recycling. If all the solvent is toluene, separation of toluene (bp=110° C.) and TMA (bp=125° C.) would be difficult.

EXAMPLE 8

Another solvent system toluene/cyclohexane (300/240) was used to dissolve TMA (200 mmol). After cooling to −25° C. water (160 mmol) was added slowly from a pump syringe. The total reaction time was about 5 hours. 53% of the original aluminum value was recovered.

EXAMPLE 9

Products from the above described experiments gave good activities in ethylene polymerization reactions. The catalyst activity was tested by polymerizing ethylene at 60 psi and 90° C. for about 10 minutes in the presence of zirconocene dichloride, in a 600 ml parr reactor. The average specific activities were between 2.2 to $4.3 \times 10^6$ g PE/mol Zr.atm hr.

The results of Examples 1 to 8 are summarized in Table 1.

TABLE 1

Mixed Solvent System
Salt Hydrate Compared to Water Hydrolysis

| Example | Solvent System | Hydrolysis Agent | TMA Mmol Al | Reaction Time (hr) | React Temp. | Recovered Al Value Mmol Al | % |
|---|---|---|---|---|---|---|---|
| 1 | Tol/Hex (150/150) | A | 200 | 24 | RT | 122 | 61 |
| 2 | Tol/Hex (150/150) | A | 200 | 2 | RT | 164 | 82 |
| 3 | Tol/Hex (300/100) | A | 1000 | 3 | RT | 802 | 80 |
| 4 | Tol/Hex (300/300) | B | 200 | 5 | −25° C. | 148 | 74 |
| 5 | Tol/Hex (300/300) | B | 200 | 20 | −25° C. | 76 | 38 |
| 6 | Tol/Hex (150/450) | B | 200 | 5 | −25° C. | 118 | 59 |
| 7 | Tol/IP (360/240) | B | 200 | 5 | −25° C. | 129 | 65 |
| 8 | Tol/Cyclohexane (300/240) | B | 200 | 5 | −25° C. | 106 | 53 |

A = $LiOH.1H_2O$
B = $H_2O$
Hex = Hexanes
IP = Isopentane
Tol = Toluene
Tol/Hex (150/450) = Toluene (150 ml) and Hexanes (450 ml)
RT = Room Temperature

What is claimed is:

1. A process for preparing a methylaluminoxane comprising the steps of (i) reacting water with a solution of an alkylaluminum compound, wherein at least about half of the alkyl groups are methyl groups, in a 1:4 to 4:1 by volume aliphatic hydrocarbon/aromatic hydrocarbon solvent mixture, wherein the aliphatic hydrocarbon solvent has a lower boiling point than the aromatic hydrocarbon solvent, so as to form a product solution of methylaluminoxane in said solvent mixture along with unreacted alkylaluminum and insoluble reaction products and (ii) separating said insoluble reaction products from said product solution.

2. A process according to claim 1 including the step of removing the aliphatic solvent from said product solution.

3. A process according to claim 1 including the step of removing the aliphatic solvent and at least a portion of the unreacted alkylaluminum compound and aromatic solvent from said product solution.

4. A process according to claim 3 including the steps of separating the removed aliphatic solvent from the removed alkylaluminum compound and removed aromatic solvent by fractional distillation and recycling the resulting solution of alkylaluminum compound in aromatic solvent to step (i) of claim 1.

5. The process of claim 1 wherein the alkylaluminum compound is trimethylaluminum.

6. The process of claim 2 wherein the alkylaluminum compound is trimethylaluminum.

7. The process of claim 4 wherein the alkylaluminum compound is trimethylaluminum.

8. The process of claim 3 wherein the boiling point of the aliphatic solvent is at least about 10° C. lower than the boiling point of said aromatic solvent.

9. The process of claim 8 wherein the aromatic solvent has from about 6 to 20 carbons and the aliphatic solvent has from about 5 to 7 carbons.

10. The process of claim 1 including the step of removing all of the solvent from the product solution following the separation of the insoluble reaction products so as to provide a solid, organic solvent soluble methylaluminoxane product.

* * * * *